(12) United States Patent
Viswanathan et al.

(10) Patent No.: US 8,348,858 B2
(45) Date of Patent: Jan. 8, 2013

(54) STENT DELIVERY GUIDE WIRE

(75) Inventors: Raju R. Viswanathan, St. Louis, MO (US); Jonathan C. Sell, Eagan, MN (US)

(73) Assignee: Stereotaxis, Inc., St. Louis, MO (US)

( * ) Notice: Subject to any disclaimer, the term of this patent is extended or adjusted under 35 U.S.C. 154(b) by 1753 days.

(21) Appl. No.: 11/325,680

(22) Filed: Jan. 4, 2006

(65) Prior Publication Data
US 2006/0270948 A1    Nov. 30, 2006

Related U.S. Application Data

(60) Provisional application No. 60/641,387, filed on Jan. 5, 2005.

(51) Int. Cl.
*A61B 5/00* (2006.01)
(52) U.S. Cl. ........................ 600/585; 604/523
(58) Field of Classification Search .................. 600/585; 604/523
See application file for complete search history.

(56) References Cited

U.S. PATENT DOCUMENTS

| | | | | |
|---|---|---|---|---|
| 5,630,427 A | * | 5/1997 | Hastings | 604/524 |
| 5,931,818 A | * | 8/1999 | Werp et al. | 604/270 |
| 6,689,119 B1 | * | 2/2004 | Di Caprio et al. | 604/523 |
| 2002/0116043 A1 | * | 8/2002 | Garibaldi et al. | 607/126 |
| 2002/0122877 A1 | * | 9/2002 | Harish et al. | 427/2.24 |
| 2003/0040671 A1 | * | 2/2003 | Somogyi et al. | 600/424 |
| 2003/0060869 A1 | * | 3/2003 | Feeser et al. | 623/1.11 |
| 2004/0133130 A1 | | 7/2004 | Ferry et al. | |
| 2005/0107867 A1 | * | 5/2005 | Taheri | 623/1.38 |
| 2005/0240120 A1 | * | 10/2005 | Modesitt | 600/585 |

* cited by examiner

*Primary Examiner* — Max Hindenburg
*Assistant Examiner* — Renee Danega
(74) *Attorney, Agent, or Firm* — Harness, Dickey & Pierce, P.L.C.

(57) ABSTRACT

A guide wire for magnetically navigating a medical device through in a subject's body comprising an elongate wire having a proximal and distal end, a portion adjacent the distal end that is more flexible than the more proximal portions of the elongate wire, and a first magnetically responsive element on the distal end of the elongate wire. The guide wire further comprises one or more magnetically responsive elements spaced apart from the first magnetically responsive element and disposed on the more flexible portion of the elongate wire. The guide wire provides for bending or deflecting the distal end of the stent, to provide easier navigation of the distal end of the guide wire and the stent through the vasculature of a subject body.

10 Claims, 4 Drawing Sheets

STENT DELIVERY GUIDE WIRE

CROSS-REFERENCE TO RELATED APPLICATIONS

This application claims the benefit of U.S. provisional patent application Ser. No. 60/641,387, filed Jan. 5, 2005, the entire disclosure of which is incorporated herein by reference.

FIELD OF THE INVENTION

This invention relates to guide wires and catheters for delivery of medical therapeutic devices within a subject's body, and more particularly to magnetically navigable guide wires and catheters for delivery of intravascular stents in a subject's body.

BACKGROUND OF THE INVENTION

Guide wire and catheter devices are commonly used to deliver medical therapy, such as stents, through the vasculature of the body to a target region. Navigation of a conventional guide wire involves rotating or applying a torque to the proximal end of the guide wire repeatedly to rotate the distal tip while the wire is pushed. This action is repeated until, by trial and error, the tip enters the desired vessel branch. In navigating guide wires in the vasculature of the body, it is desirable that the tip of the guide wire be flexible enough to negotiate the sharp turns that are necessary to reach the target area for delivery of medical therapy. However, after the guide wire has made several bends, it becomes increasingly difficult to control, often requiring repeated attempts to enter or gain access to a desired vessel branch. This trial and error method can frustrate the physician and cause additional wall contact and potential trauma to the vessel.

In addition, once a guide wire has been positioned within the subject's body, it is necessary to deliver a therapeutic device for procedures such as balloon angioplasty, atherectomy, or coronary stents. Often, a guide wire can be guided to the target site but it becomes difficult or impossible to guide a therapeutic device to the same location. This failure commonly results from the inability of stiffer balloon catheters and stent delivery systems to conform to the bends and turns of the vasculature. This problem has become very relevant due to the increased success, in recent years, of guide wire navigation to remote locations via tortuous paths.

To address some of these difficulties, magnetically navigable guide wires and balloon catheters have been developed which can be controlled with the application of an external magnetic field. An example of a magnetically navigable tether wire is disclosed in Werp et al., U.S. Pat. No. 5,931,818 (incorporated in its entirety herein by reference) and a magnetically navigable guide wire is disclosed in U.S. patent application Ser. No. 10/337,236, filed Jan. 6, 2003, for Magnetically Navigable Medical Guidewire. When the distal end of the guide wire is proximal to the branch of interest, the user operates a magnetic system to apply a magnetic field (with the aid of a computerized user interface) to deflect the wire tip into the vessel branch. This magnet system can frequently direct the distal end of the guide wire into a vessel on a first effort, eliminating the trial and error of manually operated guide wires and thereby reducing or eliminating trauma to the vessel wall. While existing magnetic guidewires are much easier to navigate than conventional guide wires, when carrying a stent the added stiffness can make navigation more difficult.

SUMMARY OF THE INVENTION

The present invention relates to magnetically navigated guide wires and delivery catheters. According to the principles of the present invention, a guide wire is provided that can be magnetically navigated in a subject's body which comprises an elongate wire having a proximal end and a distal end. A portion of the guidewire adjacent the distal end is more flexible than the more proximal portions of the elongate wire, and a first magnetically responsive element on the distal end of the elongate wire. The guide wire further comprises one or more additional magnetically responsive elements spaced apart from the first magnetically responsive element and disposed on the more flexible portion of the elongate wire. Due to its flexibility, the portion of the elongate wire adjacent the distal end carrying the magnetically responsive elements can substantially orient relative to an externally applied magnetic field. In one embodiment of the present invention, the more flexible portion adjacent the distal end of the elongate wire may comprise one or more tapered sections each having a section length and a corresponding predetermined reduction in wire cross-section along the section.

In accordance with one aspect of the invention, the guide wire is adapted to be inserted through the lumen of a stent and positioned with the one or more magnetically responsive elements extending beyond the distal end of the stent. The guide wire may also be positioned with at least one of the one or more magnetically responsive elements disposed within the lumen of the stent. The one or more magnetically responsive elements are of such material and sufficient size that the magnetic elements are capable of deflecting the distal end of the stent and guide wire to substantially orient relative to an externally applied magnetic field for guiding the stent through the body.

In accordance with another aspect of the invention, a guide element is adapted for use with a balloon or stent delivery catheter where the guide element can be loaded on to the distal end of the balloon or stent delivery catheter. The guide element comprises a sleeve having a magnetic element disposed on the distal end of the sleeve, and one or more magnetically responsive elements disposed on the proximal end of the sleeve, which is adapted to be secured to the balloon or stent delivery catheter. The guide element remains in position near the distal end of the balloon or stent delivery catheter as it is navigated through the body, and provides for magnetic navigation to steer the distal end of the balloon or delivery catheter.

Thus, various embodiments of a guide wire, guide element, and methods of use are described and claimed. A method of attaching a guide element to stent delivery catheters and delivery systems is also disclosed. Further aspects of the present invention will become apparent from the detailed description provided hereinafter. It should be understood that the detailed description and specific examples, while indicating various embodiments of the present invention, are for illustration purposes only and are not intended to limit the scope of the invention.

BRIEF DESCRIPTION OF THE DRAWINGS

Corresponding reference numerals indicate corresponding parts throughout the several views of the drawings.

DETAILED DESCRIPTION OF THE INVENTION

Figure 1:
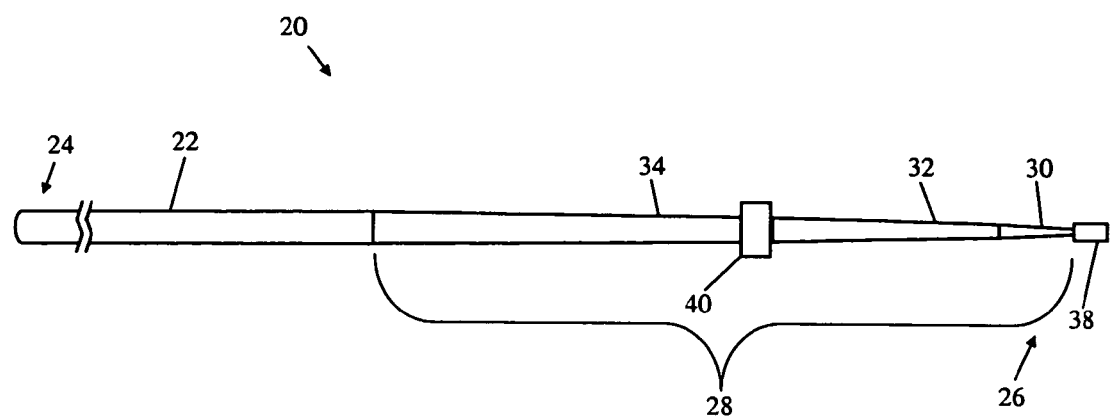
FIG. 1 is a side elevation view of a preferred embodiment of a magnetically navigable guide wire in accordance with the principles of the present invention.

A preferred embodiment of magnetically navigable guide wire in accordance with the principles of the present invention is indicated generally as 20 in FIG. 1. The guide wire 20 comprises an elongate wire 22 having a proximal end 24, a distal end 26. A portion 28 of the wire 22 adjacent the distal end is more flexible than the more proximal portions of the elongate wire. The elongate wire 22 is preferably made of a memory shaped superelastic alloys, such as nickel-titanium (nitinol), stainless steel, or other suitable flexible, biocompatible material.

In the preferred embodiment of the present invention shown in FIG. 1, the more flexible portion 28 at the distal end 26 of the elongate wire 22 may comprise one or more tapered sections 30, 32 and 34, which decrease in diameter toward their distal ends. This decrease in diameter can be uniform or non-uniform over each section. In this preferred embodiment, the most proximal section 34 tapers from a diameter of about 0.325 millimeters to a diameter of about 0.239 millimeters over a length of about 6 centimeters, the next most distal section 32 tapers from a diameter of about 0.239 millimeters to a diameter of about 0.114 millimeters over a length of about 3 centimeters, and the distal most section 30 tapers from a diameter of about 0.114 millimeters to a diameter of about 0.089 millimeters over a length of about 1 centimeter. It should be noted that the number, lengths, and tapers of the sections of this preferred embodiment are exemplary of only one preferred embodiment, and the number, length, and diameters of the tapered sections may vary without departing from the principles of this invention.

For example, the flexible section 28 may comprise just two tapered sections instead of the three sections shown in FIG. 1. In this case the more proximal section might have a diameter tapering from about 0.325 millimeters to about 0.229 millimeters over a length of about 3 centimeters, and a more distal section tapering from a diameter of about 0.229 millimeters to a diameter of about 0.076 millimeters over a length of 1 cm. Of course numerous other configurations are possible.

A first magnetically responsive element 38 is mounted at or near the distal end 26 of the wire 22. At least one additional magnetically responsive element 40 spaced apart from the first magnetically responsive element 38 and disposed on the more flexible portion 28 of the elongate wire 22. The portion of the elongate wire 22 adjacent the distal end 26 comprising the magnetically responsive elements 38 and 40 is capable of being substantially oriented relative to an externally applied magnetic field.

The magnetically responsive element 38 disposed on the distal end of the guide wire 20 is of such material and sufficient size that under the influence of an applied magnetic field of as low as 0.1 Tesla, and more preferably as low as 0.08 Tesla, and most preferably as low as 0.06 Tesla, the distal end 26 of the guide wire 20 orients with respect to the local direction of the externally applied magnetic field. The magnetically responsive elements 38 and 40 can be made of a permanent magnetic material or a permeable magnetic material. Suitable permanent magnetic materials include neodymium-iron-boron (Nd—Fe—B). Suitable permeable magnetic materials may include magnetically permeable alloys such as Hiperco. In one preferred embodiment of the invention, the magnetically responsive element 38 preferably has a length of about 0.3 centimeters and a diameter of about 0.036 centimeters.

The guide wire 20 is adapted to be inserted through the lumen of a stent, which may be carried over the guide wire just proximal to the magnetically responsive element 40 that is spaced apart from the first magnetically responsive element 38 on the more flexible portion 28 of the elongate wire 22. The magnetically responsive element 40 is of such material and sufficient size that the magnetic elements are capable of deflecting the distal end 26 of the guide wire 20 and the stent to substantially orient relative to an externally applied magnetic field. In a preferred embodiment of the present invention, the magnetically responsive element 40 is generally tubular, and has a diameter of about 1.067 millimeters and a length of 0.2 centimeters. However, the magnetically responsive element 40 may alternatively be comprised of any diameter and length suitable for enabling the deflection of the distal end 26 by an externally applied magnetic field.

The guide wire 20 of this preferred embodiment of the present invention is preferably of a diameter that allows the guide wire 20 to be compatible with 0.356 millimeter (0.014 inch) stent placement catheter systems, and preferably does not have a profile larger than 1.143 millimeters to match the profile of current stent systems. The magnetically responsive elements 38 and 40 may be formed of a permanent magnet material such as neodymium-iron-boron (Nd—Fe—B), or could also be formed of a magnetically permeable material, such as Hiperco, or other suitable material. The magnetically responsive elements on the guide wire 20 of this embodiment are capable of deflecting the distal end 26 of the guide wire 20 to navigate the guide wire and a stent through the body.

Figure 2:
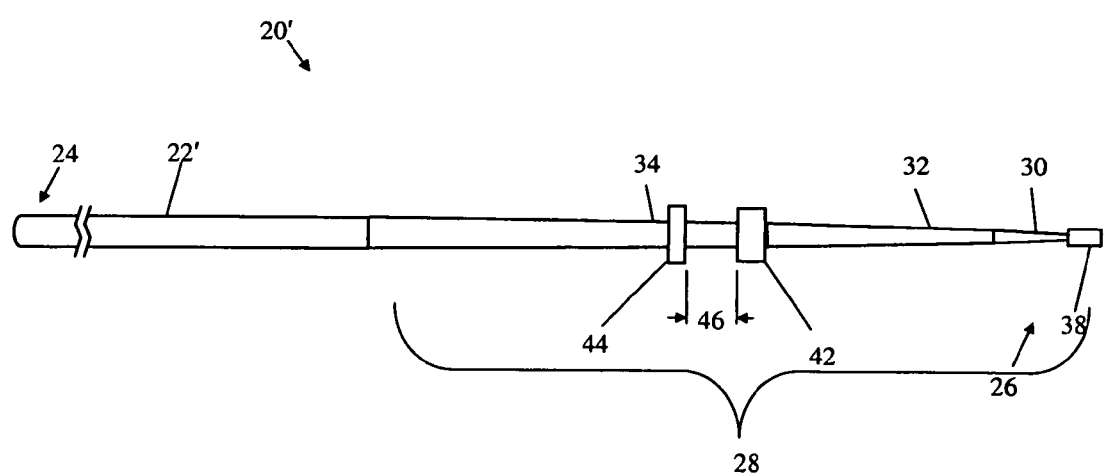
FIG. 2 is a side elevation view of another preferred embodiment of a guide wire in accordance with the principles of this invention.

A guide wire 20', in accordance with another preferred embodiment of this invention is shown in FIG. 2. Guide wire 20' is similar to guide wire 20, and corresponding reference numerals indicate corresponding parts throughout the drawings. However instead of a single additional magnetically responsive element 40, guide wire 20' has multiple additional magnetically responsive elements.

As shown in FIG. 2, the guide wire 20' comprises an elongate wire 22' having a proximal end 24, a distal end 26. A portion 28 of the wire 22' adjacent the distal end is more flexible than the more proximal portions of the elongate wire. The elongate wire 22' is preferably made of a memory shaped superelastic alloy, such us nickel-titanium (nitinol), stainless steel, or other suitable biocompatible material. A first magnetically responsive element 38 is mounted at or near the distal end 26 of the wire 22'.

As shown in FIG. 2, the elongate wire 22', and at least the section 28, preferably tapers toward the distal end. In this preferred embodiment section 28 comprises three sections 30, 32, and 34. The most proximal section 34 tapers from a diameter of about 0.325 millimeter to a diameter of about 0.249 millimeters over a length of about 6 centimeters. The next most distal section 32 tapers from a diameter of about 0.249 millimeters to a diameter of about 0.114 millimeters over a length of about 3 centimeters. The distal most section 30 tapers from a diameter of about 0.114 to about 0.076 millimeters over a length of about 1 centimeter. The distal sections are designed to be able to support, when the sections are bent or deflected by an external magnetic field of about 0.08 T, stent catheters, angioplasty catheters or other medical devices that are conventionally delivered over a supporting guide wire. This is accomplished by suitably designing the tapers such that the effective stiffness over the distal 2-6 cm is large enough to be able to support such delivered devices.

At least two additional magnetically responsive elements 42 and 44 are provided on the section 28 of the elongate wire 22', spaced apart from the first magnetically responsive element 38, and spaced from each other by a portion 46 of the proximal most section 34. The portion of the elongate wire 22' adjacent the distal end 26 comprising the magnetically responsive elements is capable of being substantially aligned relative to an externally applied magnetic field.

The magnetically responsive element 38 disposed on the distal end of the guide wire 20' is of such material and sufficient size, that under the influence of an applied magnetic field of as low as 0.1 Tesla, and more preferably as low as 0.08 Tesla, and most preferably as low as 0.06 Tesla, the distal end 26 of the guide wire 20 orients with respect to the local direction of an externally applied magnetic field. The magnetically responsive elements 38, 42 and 44 can be made of a permanent magnetic material or a permeable magnetic material. Suitable permanent magnetic materials include neodymium-iron-boron (Nd—Fe—B). Suitable permeable magnetic materials may include high magnetic permeability alloys such as Hiperco. In one preferred embodiment of the invention, the magnetically responsive element 38 preferably has a length of about 0.3 centimeters and a diameter of about 0.036 centimeters.

The guide wire 20' of this embodiment is adapted to be inserted through the lumen of a stent that may be carried just proximal to the magnetically responsive elements 42 and 44, which also provide for deflection of the distal end of the guide wire 20 and stent. The one or more magnetically responsive elements 42 and 44 are of such material and sufficient size that the magnetic elements are capable of deflecting the distal end of the stent and guide wire to substantially align relative to an externally applied magnetic field for guiding the stent through the body. In this embodiment, the magnetically responsive elements 42 and 44 each have a diameter of about 1.067 millimeters and a length of 0.2 centimeters, and are spaced apart from each other by a length 46 of about 1 centimeter. However, the magnetically responsive elements 42 and 44 may alternatively be comprised of any diameter and length suitable for enabling the deflection of the distal end of the guide wire 20' and the stent.

Figure 3:
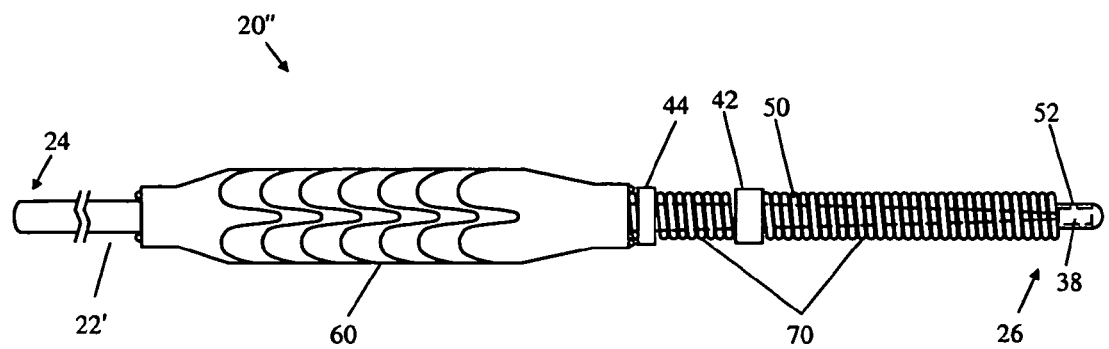
FIG. 3 is a side elevation view of another preferred embodiment of a guide wire, showing a stent carried thereon.

Another preferred embodiment of a guide wire in accordance with the principles of this invention is indicated generally as 20" in FIG. 3. Guide wire 20" is similar in construction to guide wire 20' and corresponding parts are identified with corresponding reference numerals. However, guide wire 20" further comprises a coiled wire 50 disposed over at least the distal portions of the elongate wire 22' between the magnetically responsive element 44 and the magnetically responsive element 38. The coiled wire 50 is preferably made of a radiopaque material, such as platinum, useful for viewing in an X-ray or fluoroscopic imaging system. The magnetically responsive element 38 on the distal end 26 is preferably encapsulated by a polymer coating 52.

As shown in FIG. 3, the guide wire 20" is adapted to carry a stent 60, with the distal end of the stent 60 just proximal to the magnetically responsive element 44. The guide wire 20" preferably has a diameter of between about 0.011 inches and about 0.035 inches, and is preferably of a diameter that allows the guide wire 20" to be compatible with and used in 0.356 millimeter (0.014 inch) stent placement catheter systems, and preferably does not have a profile larger than 1.143 millimeters to match the profile of current stent systems. It should be noted that the magnetically responsive elements 42 and 44 may ideally be of a diameter that will allow the stent 60 to be carried or positioned with at least one or more of the magnetically responsive elements 42 and 44 disposed within the lumen of the stent. In addition, the distal section of the wire possesses sufficient stiffness to provide good delivery support for devices such as stent catheters and balloon catheters that are delivered over the wire.

Figure 4:
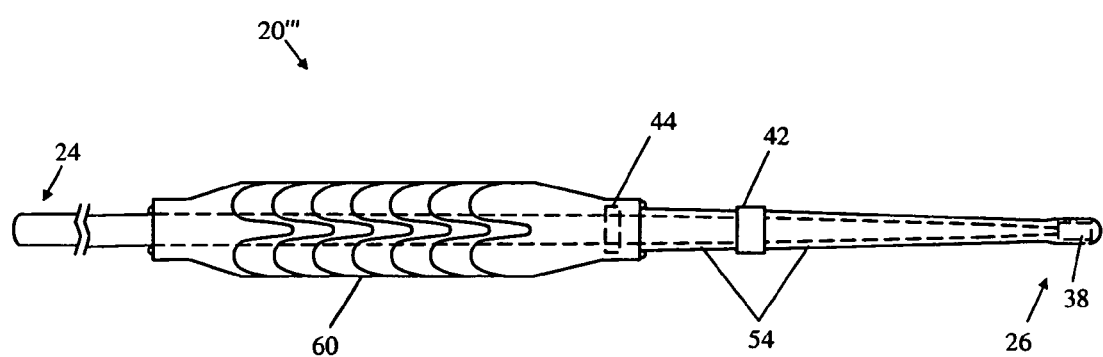
FIG. 4 is a side elevation view of yet another preferred embodiment of a guide wire and stent in accordance with the principles of the present invention.

Another preferred embodiment of a guide wire in accordance with the principles of this invention is indicated generally as 20''' in FIG. 4. The guide wire 20''' is similar in construction to guide wire 20' and corresponding parts are identified with corresponding reference numerals. However, guide wire 20''' further comprises a urethane or other polymer coating 54, which is preferably loaded with radiopaque material to facilitate viewing of the guide wire 20''' in an X-ray or fluoroscopic imaging system. Platinum or other suitable material may be used to provide the radiopaque imaging capability. The polymer may also be loaded with a magnetically responsive material, such as Hiperco material, to increase the amount of magnetically responsive material to facilitate orientation of the distal end of the medical device in response to an externally applied magnetic field. The biocompatible polymer coating 54 also encapsulates the magnetic elements 38, 42 and 44. The magnetically responsive elements 42 and 44 shown in FIG. 4 are ideally of a diameter that will allow the stent 60 to be carried or positioned over the magnetically responsive element 44. Alternatively, the stent 60 may be carried over one or more magnetically responsive elements, which may be positioned within the opening or lumen of the stent 60 to assist in deflecting the end of the stent for improving navigation of the stent through the subject's body. The guide wire 20''' in accordance with the principles of the present invention therefore provides for bending or deflecting the distal end of the stent, to provide easier navigation of the distal end 26 of the guide wire 20''' and the stent 60 through the vasculature of a subject body.

Figure 5A:
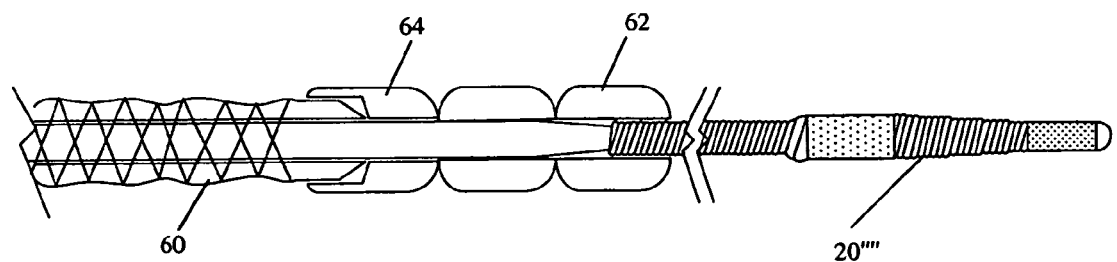
FIG. 5A is a side elevation view of a guide wire and stent, showing a slotted configuration for the magnetically responsive elements that can be used to position magnets along the length of the guide wires of the various embodiments of this invention.
Figure 5B:
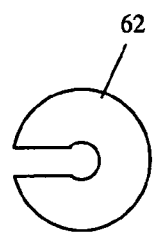
FIG. 5B is a transverse cross-sectional view of a slotted magnet configured for attaching to guidewires shown in FIG. 5A.

In yet another embodiment of the invention shown in FIG. 5A, a stent delivery device 20'''' including a stent 60 is shown with one or more slotted magnetically responsive elements 62 mounted onto the delivery device near the distal end. The magnetically responsive elements 62 have a generally cylindrical shape, and comprise a slot in the side of the cylindrical shape that extends approximately to the axial center of the magnetic element. The slotted magnetic elements are adapted to attached securely to the stent delivery device 20'''' near the distal end, where the magnetically responsive elements 62 are capable of substantially aligning the distal end of the delivery catheter within a subject body with an applied magnetic field. The magnetically responsive elements 62 disposed on the stent delivery device 20'''' are of such material and sufficient size, that under the influence of an applied magnetic field of as low as 0.1 Tesla, and more preferably as low as 0.08 Tesla, the distal end of the stent delivery device 20'''' substantially aligns relative to the local applied magnetic field direction. The magnetically responsive element 62 can be made of a permanent magnetic material or a permeable magnetic material. Suitable permanent magnetic materials may include neodymium-iron-boron (Nd—Fe—B). Suitable permeable magnetic materials may include high magnetic permeability alloys such as Hiperco. In one embodiment of the present invention, the slotted magnetically responsive elements 62 shown in FIG. 5B have a diameter of about 1.07 millimeters, a length of between 1.5 and 3.5 millimeters, and a slot of about 0.35 millimeters in width. The elements 62 preferably have a center opening that is slightly larger than the slot for receiving and engaging the stent delivery device 20''''.

A proximally-mounted magnetically responsive element 64 may further comprise a cavity in one end to receive the end of the stent delivery device as shown in FIG. 5A. In another embodiment, the magnetically responsive elements 62 could have a through hole (rather than a slit) for threading the wire through, and secured to the wire by a suitable adhesive or weld.

Figure 6:
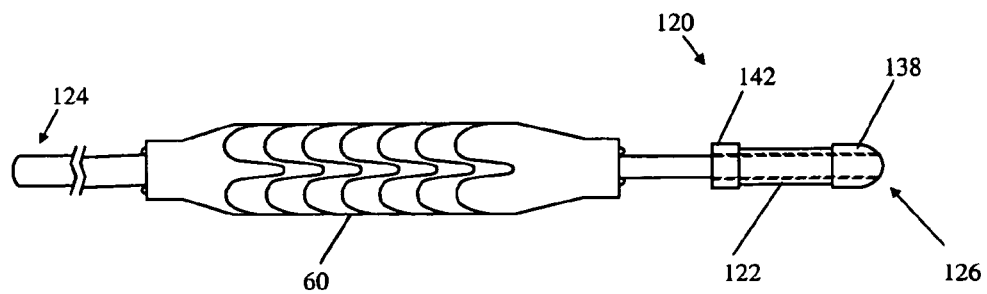
FIG. 6 is a cross-section of a guide element that is adapted to be secured to a balloon or stent delivery guide catheter in accordance with the principles of this invention.

In yet another embodiment of the invention shown in FIG. 6, a guide element 120 is provided having a flexible sleeve 122 and a magnetically responsive element 138 disposed on the distal end 126 of the sleeve 122, and one or more magnetically responsive elements 142 disposed on the proximal end of the sleeve 122, which is adapted to be secured to the balloon or stent delivery catheter 124 (for example by friction fit or bayonette or threaded connection or by adhesive). The guide element 120 provides for magnetic navigation of the distal end of a balloon or stent delivery catheter in the same manner as in the guide wire embodiments above. The proximal end of the sleeve 120 covers at least a portion of the distal end of the medical device that it is adapted to be secured to, and may be secured by an adhesive or by a press fit. The magnetically responsive element 138 disposed on the distal end of the sleeve 120 is of such material and sufficient size, that under the influence of an applied magnetic field of as low as 0.1 Tesla, and more preferably as low as 0.08 Tesla, the distal end of the delivery catheter device and guide element 120 substantially aligns with the local applied magnetic field direction. The magnetically responsive element 138 can be made of a permanent magnetic material or a permeable magnetic material. Suitable permanent magnetic materials may include neodymium-iron-boron (Nd—Fe—B). Suitable permeable magnetic materials may include high magnetic permeability alloys such as Hiperco. In the one embodiment of the invention, the magnetically responsive element 138 preferably has a length of about 0.3 centimeters and a diameter of about 0.036 centimeters. The magnetically responsive element 138 may alternatively be comprised of any material and length suitable for enabling the deflection of the distal end of a delivery catheter by an externally applied magnetic field for guiding the distal end through the vasculature of the body.

The second magnetically responsive element 142 shown in FIG. 6 is spaced apart from the first magnetically responsive element 138, preferably by between 5 and 10 millimeters. The magnetically responsive element 142 is of such material and sufficient size that the magnetic elements are capable of deflecting the distal end of the delivery catheter 124 to substantially orient with an externally applied magnetic field. In one embodiment of the present invention, the magnetically responsive element 142 is generally tubular, and has a diameter of about 1.067 millimeters and a length of about 0.2 centimeters. However, the magnetically responsive element 142 may alternatively be any diameter and length suitable for enabling the deflection of the distal end of the stent delivery catheter by an externally applied magnetic field. The guide element 120 of this embodiment of the present invention preferably has a diameter of between about 0.011 inches and about 0.035 inches, and is preferably of a diameter that allows the guide element 120 to be compatible with 0.356 millimeter (0.014 inch) stent placement catheter systems, and preferably does not have a profile larger than 1.143 millimeters to match the profile of current stent delivery systems. The magnet may be formed of a permanent magnet material such as neodymium-iron-boron (Nd—Fe—B), or could also be formed of a magnetically permeable material, such as Hiperco, or other suitable material. The guide element 120 is capable of being magnetically deflected to guide the distal end of the delivery catheter through the body.

Figure 7:
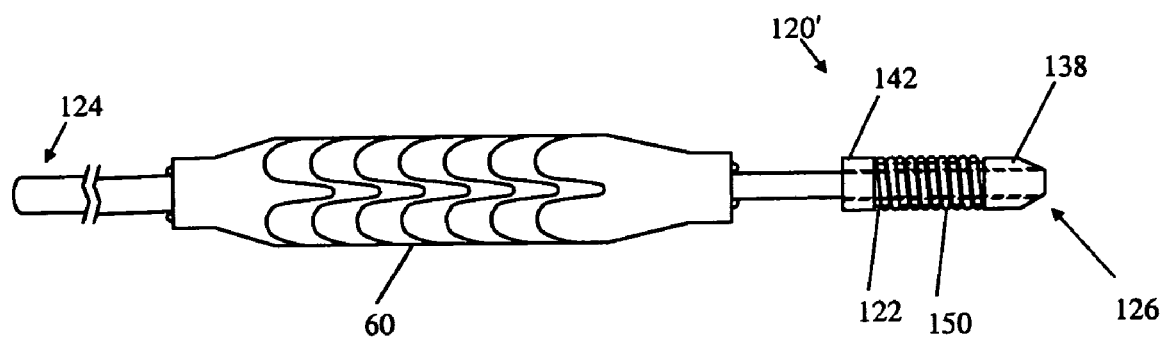
FIG. 7 is a side elevation view of a balloon or stent delivery guide catheter showing another preferred embodiment of a guide element that is adapted to be secured to a balloon or stent delivery guide catheter.

Yet another embodiment of the guide element for a delivery guide catheter is shown in FIG. 7, which is similar in construction to the embodiment shown in FIG. 6. In the embodiment shown in FIG. 7, the sleeve 122 of the guide element 120' further comprises a stainless steel or Hiperco wound coil 150. It should be noted that the wound coil 150 could be encapsulated in a polymer layer surrounding the sleeve 122, or the embodiment could alternately comprise a polymer layer loaded with Hiperco material. The magnetically responsive element 138' on the distal end of the sleeve 120 may also comprise a tapered shape as shown in FIG. 7. The proximal end of the guide element 120' may be configured to snap onto the distal end of a delivery catheter as shown, or may be alternately secured by an adhesive or other bonding means.

The advantages of the above described embodiment and improvements should be readily apparent to one skilled in the art, as to enabling delivery of a stent with a subject body using a magnetically navigable guide wire. Additional design considerations may be incorporated without departing from the spirit and scope of the invention. Accordingly, it is not intended that the invention be limited by the particular embodiment or form described above, but by the appended claims.

What is claimed:

1. A guide wire having a distal end that can be magnetically navigated in a subject's body and can be used to guide a medical device through the subject's body, the guide wire comprising:

an elongate wire core having a proximal end, a distal end, and a portion adjacent the distal end that is more flexible than the more proximal portions of the elongate wire;

a first magnetically responsive element on the distal end of the elongate wire of such material and sufficient size to substantially align the distal end of the elongate wire relative to an externally applied magnetic field; and one or more magnetically responsive elements spaced apart from the first magnetically responsive element and disposed on the more flexible portion of the elongate wire, the one or more magnetically responsive elements being of such material and sufficient size to substantially align the flexible portion of the elongate wire relative to an externally applied magnetic field, wherein said one or more magnetically responsive elements includes at least a second magnetically responsive element separated from the first magnetically responsive element by a spacing of between about 4 and 10 millimeters, wherein the guide wire is adapted to be inserted through the lumen of a stent and positioned with the one or more magnetically responsive elements extending beyond the distal end of the stent.

2. The guide wire of claim 1, wherein the one or more magnetically responsive elements on the more flexible portion of the elongate wire may be positioned adjacent the distal end of the stent in a manner such that the one or more magnetically responsive elements are capable of deflecting the distal end of the stent to substantially align relative to an externally applied magnetic field for guiding the stent through a subject's body.

3. A guide wire having a distal end that can be magnetically navigated in a subject's body and can be used to guide a medical device through the subject's body, the guide wire comprising:
an elongate wire core having a proximal end, a distal end, and a portion adjacent the distal end that is more flexible than the more proximal portions of the elongate wire;
a first magnetically responsive element on the distal end of the elongate wire of such material and sufficient size to substantially align the distal end of the elongate wire relative to an externally applied magnetic field; and
one or more magnetically responsive elements spaced apart from the first magnetically responsive element and disposed on the more flexible portion of the elongate wire, the one or more magnetically responsive elements being of such material and sufficient size to substantially align the flexible portion of the elongate wire relative to an externally applied magnetic field,
wherein said one or more magnetically responsive elements includes at least a second magnetically responsive element separated from the first magnetically responsive element by a spacing of between about 4 and 10 millimeters,
wherein the guide wire is adapted to be inserted through the lumen of a stent and positioned with one or more of the magnetically responsive elements within the lumen of the stent, such that the magnetically responsive elements are capable of deflecting the distal end of the stent to substantially align relative to an externally applied magnetic field for guiding the stent through a subject's body.

4. A guide wire having a distal end that can be magnetically navigated in a subject's body and can be used to guide a medical stent device through the subject's body, the guide wire comprising:
an elongate core wire having a proximal end, a distal end, and a portion adjacent the distal end that is more flexible than the more proximal portions of the elongate wire;
a first magnetically responsive element on the distal end of the elongate core wire of such material and sufficient size to substantially align the distal end of the elongate core wire relative to an externally applied magnetic field; and
a second magnetically responsive element spaced apart from the first magnetically responsive element and disposed on the more flexible portion of the elongate core wire, the second magnetically responsive element being separated from the first magnetically responsive element by a spacing of between about 4 and 10 millimeters, and made of such material and sufficient size to substantially align the flexible portion of the elongate wire relative to an externally applied magnetic field,
wherein the guide wire is adapted to be inserted through the lumen of a stent and positioned with the second magnetically responsive element on the more flexible portion of the elongate wire extending beyond the distal end of the stent.

5. A guide wire having a distal end that can be magnetically navigated in a subject's body and can be used to guide a medical stent device through the subject's body, the guide wire comprising:
an elongate core wire having a proximal end, a distal end, and a portion adjacent the distal end that is more flexible than the more proximal portions of the elongate wire;
a first magnetically responsive element on the distal end of the elongate core wire of such material and sufficient size to substantially align the distal end of the elongate core wire relative to an externally applied magnetic field; and
a second magnetically responsive element spaced apart from the first magnetically responsive element and disposed on the more flexible portion of the elongate core wire, the second magnetically responsive element being separated from the first magnetically responsive element by a spacing of between about 4 and 10 millimeters, and made of such material and sufficient size to substantially align the flexible portion of the elongate wire relative to an externally applied magnetic field,
wherein the guide wire is adapted to be inserted through the lumen of a stent and positioned with the second magnetically responsive element within the lumen of the stent, such that the second magnetically responsive element is capable of deflecting the distal end of the stent to substantially align relative to an externally applied magnetic field for guiding the stent through a subject's body.

6. A guide wire having a distal end that can be magnetically navigated in a subject's body for delivering a stent device to a target location in the subject body, the guide wire comprising:
an elongate wire having a proximal end, a distal end, and a portion adjacent the distal end that is more flexible than the more proximal portions of the elongate wire;
a first magnetically responsive element on the distal end of the elongate wire of such material and sufficient size to substantially align the distal end of the elongate wire relative to an externally applied magnetic field; and
a second magnetically responsive element on the more flexible portion of the elongate wire, the second magnetically responsive element being separated from the first magnetically responsive element by a spacing of between about 4 and 10 millimeters, such that the first and second magnetically responsive elements separated by a spacing of between about 4 and 10 millimeters together act as a guide element capable of deflecting the distal end of the device to substantially orient the distal end with the direction of an external magnetic field,
wherein the guide wire is adapted to be inserted within the lumen of a stent and positioned with the second magnetically responsive element on the more flexible portion of the elongate wire extending beyond the distal end of the stent.

7. The guide wire of claim 6, wherein the second magnetically responsive element is adjustably positionable adjacent the distal end of the stent in a manner such that the second magnetically responsive element is capable of deflecting the distal end of the stent to substantially align relative to an externally applied magnetic field for guiding the stent through the subject body.

8. The guide wire of claim 7 where at least one of the one or more magnetically responsive elements is made from cylindrical permanent magnet material having a through-hole along its length which is sized to allow it to be positioned along the length of the guide wire core at a distance of between 4 and 10 millimeters from the first magnetically responsive element.

9. The guide wire of claim 7 where the at least one of the one or more magnetically responsive elements is made from cylindrical permanent magnet material having a slot along its length in the side of the cylindrical shape that extends approximately to the axial center of the magnetically responsive element, where the slot is sized to allow the magnetic element to be positioned along the length of the guide wire core.

10. The guide wire of claim 7 wherein the flexible portion of the elongate wire comprises a tapered section that reduces in cross-section along the distal direction over a predetermined length at the distal end of the elongate wire.

* * * * *